US008604076B2

(12) United States Patent
Rimpler et al.

(10) Patent No.: US 8,604,076 B2
(45) Date of Patent: Dec. 10, 2013

(54) METHOD FOR PRODUCING A PHARMACEUTICAL COMPOSITION COMPRISING ROTIGOTINE

(75) Inventors: Stephan Rimpler, Hilden (DE); Sabine Grapatin, Langenfeld (DE); Cliff Krein, Overath (DE); Markus Thelen, Monheim (DE)

(73) Assignee: UCB Pharma GmbH, Monheim (DE)

( * ) Notice: Subject to any disclaimer, the term of this patent is extended or adjusted under 35 U.S.C. 154(b) by 1089 days.

(21) Appl. No.: 10/344,884

(22) PCT Filed: Aug. 21, 2001

(86) PCT No.: PCT/EP01/09595
§ 371 (c)(1),
(2), (4) Date: Feb. 11, 2003

(87) PCT Pub. No.: WO02/15903
PCT Pub. Date: Feb. 28, 2002

(65) Prior Publication Data
US 2003/0166709 A1 Sep. 4, 2003

(30) Foreign Application Priority Data

Aug. 24, 2000 (DE) .................................. 100 41 479

(51) Int. Cl.
*A01N 43/06* (2006.01)
*A61K 31/38* (2006.01)

(52) U.S. Cl.
USPC ............................................................ 514/447

(58) Field of Classification Search
USPC ............................................. 514/438, 447
See application file for complete search history.

(56) References Cited

U.S. PATENT DOCUMENTS

| | | | | |
|---|---|---|---|---|
| 2,964,448 A | * | 12/1960 | Anschel | 514/12.1 |
| 2,992,165 A | * | 7/1961 | Thompson | 514/10.8 |
| 4,056,635 A | * | 11/1977 | Glen et al. | 514/731 |
| 4,465,692 A | | 8/1984 | Horn | 424/330 |
| 4,540,691 A | | 9/1985 | Horn | 514/211 |
| 4,564,628 A | * | 1/1986 | Horn | 514/438 |
| 4,722,933 A | | 2/1988 | Horn | 514/438 |
| 4,743,618 A | | 5/1988 | Horn | 514/438 |
| 4,772,933 A | | 9/1988 | Schade | 357/63 |
| 4,885,308 A | | 12/1989 | Horn | 514/438 |
| 4,913,699 A | | 4/1990 | Parsons | 604/68 |
| 5,176,643 A | * | 1/1993 | Kramer et al. | 604/135 |
| 5,177,112 A | | 1/1993 | Horn | 514/654 |
| 5,234,945 A | * | 8/1993 | Belluzzi | 514/438 |
| 5,256,661 A | | 10/1993 | Horn | 514/248 |
| 5,382,596 A | | 1/1995 | Sleevi et al. | 514/459 |
| 5,486,611 A | | 1/1996 | Lin et al. | 546/62 |
| 5,519,034 A | | 5/1996 | Kozlik et al. | 514/307 |
| 5,545,755 A | | 8/1996 | Lin et al. | 564/428 |
| 5,614,518 A | | 3/1997 | Leeson et al. | 514/234.5 |
| 5,633,376 A | | 5/1997 | Thurkauf et al. | 544/360 |
| 5,658,955 A | | 8/1997 | Hitzig | 514/654 |
| 5,670,501 A | | 9/1997 | Peck et al. | 514/234.2 |
| 5,681,956 A | | 10/1997 | Thurkauf et al. | 544/295 |
| 5,840,062 A | | 11/1998 | Gumaste et al. | 604/68 |
| 5,981,524 A | | 11/1999 | Peck et al. | 514/234.2 |
| 6,057,371 A | | 5/2000 | Glennon | 514/649 |
| 6,066,292 A | * | 5/2000 | Purwar | 422/1 |
| 6,153,653 A | * | 11/2000 | Shashoua | 514/642 |
| 6,166,037 A | * | 12/2000 | Budhu et al. | 514/326 |
| 6,218,421 B1 | | 4/2001 | King | 514/421 |
| 6,299,900 B1 | * | 10/2001 | Reed et al. | 424/449 |
| 6,300,365 B1 | | 10/2001 | Holman | 514/418 |
| 6,372,920 B1 | | 4/2002 | Minaskanian et al. | 549/75 |
| 6,498,196 B1 | | 12/2002 | Roberts et al. | 514/712 |
| 6,576,649 B1 | * | 6/2003 | Kis | 514/324 |
| 6,620,429 B1 | | 9/2003 | Müller | 424/449 |
| 6,740,659 B2 | | 5/2004 | Brotchie | 514/280 |
| 6,844,368 B1 | | 1/2005 | Roberts et al. | 514/657 |
| 6,884,434 B1 | | 4/2005 | Müller et al. | 424/487 |
| 7,038,085 B2 | | 5/2006 | Rariy et al. | 564/165 |
| 7,087,247 B2 | | 8/2006 | Li et al. | 424/499 |
| 7,309,497 B2 | | 12/2007 | Rimpler et al. | 424/422 |
| 7,413,747 B2 | | 8/2008 | Mueller et al. | 424/448 |

(Continued)

FOREIGN PATENT DOCUMENTS

| | | | |
|---|---|---|---|
| CA | 2382648 | 3/2001 | ........... A61K 31/195 |
| CA | 2532804 | 2/2005 | ........... A61K 31/135 |
| CA | 2532859 | 2/2005 | ........... A61K 31/381 |
| CA | 2547820 | 6/2005 | ........... A61K 31/135 |
| CA | 2546797 | 7/2005 | ........... A61K 31/381 |
| CA | 2568850 | 2/2006 | ........... A61K 31/496 |
| DE | 4325855 | 2/1995 | ............. C07D 11/70 |
| EP | 0 230 629 | 8/1987 | ............. A61K 31/38 |
| EP | 0230629 | * 8/1987 | |
| EP | 0 168 505 | 8/1989 | |

(Continued)

OTHER PUBLICATIONS

DERWENT Abstract of WO89/03671.*
Complete translation of JP8903671 ("Iwata" reference).*
Translation of WO89/03671.*
Susan Hovorka & Christian Schoneich, Oxidative Degradation of Pharmaceuticals: Theory, Mechanisms and Inhibition, 90 J Pharma. Sci. 253, 261 (Mar. 2001).*
AADAC (2004) Beyond the ABCs: Amphetamines.
Barfknecht et al. (1973) J. of Medicinal Chemistry16(7): 804-808.
Belluzzi et al. (1994) Movement Disorders 9(2): 147-154.
Borsini et al (1988) Eur. J. Pharmacol 148(3): 301-307.

(Continued)

*Primary Examiner* — Sean Basquill
(74) *Attorney, Agent, or Firm* — Harness, Dickey & Pierce, P.L.C.

(57) ABSTRACT

Pharmaceutical compositions are provided for administration of rotigotine in depot form. Pharmaceutical compositions of the invention can provide therapeutically significant plasma levels of rotigotine over a period of at least 24 hours after administration to a patient. Preferred pharmaceutical compositions of the invention include oily suspensions that contain rotigotine in solid form as well as anhydrous pharmaceutical compositions that comprise rotigotine.

9 Claims, 6 Drawing Sheets

(56) References Cited

U.S. PATENT DOCUMENTS

| | | | |
|---|---|---|---|
| 2003/0026830 A1 | 2/2003 | Lautertback et al. | 424/449 |
| 2003/0027793 A1 | 2/2003 | Lautertback et al. | 514/63 |
| 2004/0034083 A1 | 2/2004 | Stephenson et al. | 514/406 |
| 2004/0048779 A1 | 3/2004 | Schollmayer | 514/2 |
| 2004/0081683 A1 | 4/2004 | Schacht et al. | 424/449 |
| 2004/0116537 A1 | 6/2004 | Li et al. | 514/663 |
| 2004/0137045 A1 | 7/2004 | Breitenbach et al. | 424/449 |
| 2004/0142904 A1 | 7/2004 | Rariy et al. | 514/63 |
| 2004/0209861 A1 | 10/2004 | Benavides et al. | 514/210.01 |
| 2005/0032873 A1 | 2/2005 | Hatzenbuhler et al. | 514/414 |
| 2005/0033065 A1 | 2/2005 | Mueller et al. | 549/74 |
| 2005/0079206 A1 | 4/2005 | Schacht et al. | 424/449 |
| 2005/0175678 A1 | 8/2005 | Breitenbach | 424/449 |
| 2005/0182090 A1 | 8/2005 | Mierau et al. | 514/304 |
| 2005/0197385 A1 | 9/2005 | Scheller et al. | 514/438 |
| 2005/0260254 A1 | 11/2005 | Breitenbach et al. | 424/449 |
| 2006/0263419 A1 | 11/2006 | Wolff | 424/448 |
| 2007/0072917 A1 | 3/2007 | Scheller et al. | 514/357 |
| 2007/0093546 A1 | 4/2007 | Scheller et al. | 514/447 |
| 2007/0191308 A1 | 8/2007 | Kramer | 514/60 |
| 2007/0191470 A1 | 8/2007 | Scheller | 514/438 |
| 2007/0197480 A1 | 8/2007 | Scheller et al. | 514/114 |
| 2008/0008748 A1 | 1/2008 | Beyreuther et al. | 424/449 |
| 2008/0138389 A1 | 6/2008 | Muller et al. | 424/448 |
| 2008/0146622 A1 | 6/2008 | Scheller et al. | 514/357 |
| 2008/0274061 A1 | 11/2008 | Schollmayer et al. | 424/45 |
| 2009/0143460 A1 | 6/2009 | Wolff et al. | 514/438 |

FOREIGN PATENT DOCUMENTS

| | | | | |
|---|---|---|---|---|
| EP | 0 651 997 | | 5/1995 | A06K 9/20 |
| ES | 002005163 | | 3/1989 | C07D 333/38 |
| ES | 002005164 | | 3/1989 | C07D 409/12 |
| GB | 2 105 589 A | | 3/1983 | A61K 9/10 |
| GB | 2 232 082 A | | 12/1990 | A61K 31/43 |
| WO | WO89/03671 | * | 5/1989 | A61K 9/10 |
| WO | 8912445 | * | 12/1989 | |
| WO | WO89/12445 | | 12/1989 | A61K 31/34 |
| WO | 9013294 | * | 11/1990 | |
| WO | WO90/13294 | | 11/1990 | A61K 31/44 |
| WO | WO93/23035 | | 11/1993 | A61K 31/40 |
| WO | WO 94/07468 | | 4/1994 | |
| WO | WO 94/09848 | | 5/1994 | |
| WO | 9729735 | * | 8/1997 | |
| WO | WO97/29735 | | 8/1997 | A61K 7/42 |
| WO | WO89/03671 | * | 10/1998 | A61K 9/10 |
| WO | 9949844 | * | 10/1999 | |
| WO | 9949852 | * | 10/1999 | |
| WO | 0113903 | * | 3/2001 | |
| WO | WO 01/38321 A1 | | 5/2001 | |
| WO | WO2006/050976 | | 3/2006 | C07D 471/04 |

OTHER PUBLICATIONS

Chan et al. (2004) Hospital Pharmacist 11: 18-22.
Chandler et al. (1990) Neuroscience 38(2): 437-445.
Chaudhuri (2002) Eur. J. Neurology 9(3): 40-43.
Corsini et al. (1981) Biological Psychiatry: 742-745.
De Ceballos et al (1985) Eur. J. Pharmacol. 116(3): 257-262.
Diggory et al. (1984) Eur. J. Pharmacol. 105(3-4): 257-263.
Duterte-Boucher et al. (1988) Eur. J. Pharmcaol. 154(2): 185-190.
Gnegy et al. (1980) Neuropharmacology 19: 319-323.
Goodwin et al. (1987) Psychopharmacology (Berl) 91(4): 500-505.
Grippo et al. (2005) Psychopharmacology (Berl) 179(4): 769-780.
Gstimer (1973): 292-293 (In German with translation).
Hacksell et al. (1979) J. Medicinal Chemistry; 22(12): 1469-1475.
Holcomb et al. (1982) Eur. J. Pharmacol. 82(3-4): 173-178.
International Preliminary Examination Report for PCT/EP2001/09595.
International Search Report for PCT/EP01/09595.
Kamata et al. (1984) Life Sciences 34(24): 2419-2427.
Liu et al. (1993) J. Med. Chem. 36: 4221-4229.
Löschmann et al. (1989) Eur. J. Pharmacology; 166: 373-380.
Mackonochie (2003) IDrugs 6(5): 420-422.
Mouradian et al. (1989) Current Opinion in Neurology and Neurosurgery; 2: 309-313.
Mucke (2003) IDrugs 6(9): 894-899.
Piercey et al. (1990) Eur. J. Pharmacol. 182(2): 219-226.
Schäfers et al. (2003) Pain 104: 579-588.
Scheller et al. (2005) EFNS Conference, "Continuous Administration of Rotigotine Does Not Induce Dyskinesia in a Rat Model of Parkinson's Disease".
Serra et al. (1981) Eur. J. Pharmacol. 72(1): 131-135.
Sonesson et al. (1993) J. Med. Chem. 36: 3409-3416.
Sonesson et al. (1995) J. Med. Chem. 38: 1319-1329.
Stichel et al. (2005) EFNS Conference, "Rotigotine Prevents Neurodegeneration in a Mouse Model of Parkinson's Disease".
Stockmeier et al. (1997) Neuropsychopharm. 16(2): 162-173.
Swart and Zeeuw (1992) Pharrmazie 47(8): 613-615.
Swart et al. (1993) Toxicology Methods; 3(4): 279-290.
Swart et al. (1995) Pharmaceutical Sciences 1: 437-440.
Timmerman et al. (1989) Eur. J. Pharmacology; 162: 143-150.
Timmerman et al. (1990) Eur. J. Pharmacology; 181: 253-260.
van Gaalen et al. (2002) Genes Brain Behav 1(3): 174-177.
Walters et al. (1994) J. Pharmac. Sci. 83(5): 758-760.
Van der Weide, et al. (1988) "The enantiomers of the D-2 dopamine receptor agonist N-0437 discriminate between pre- and postsynaptic dopamine receptors." Eur J Pharmacol 146:319-326.
Office Action, dated Apr. 20, 2004 issued in U.S. Appl. No. 10/139,894.
Office Action, dated Dec. 28, 2004 issued in U.S. Appl. No. 10/139,894.
Office Action, dated Jun. 16, 2005 issued in U.S. Appl. No. 10/139,894.
Office Action, dated Nov. 19, 2003 issued in U.S. Appl. No. 10/139,894.
Office Action, dated Apr. 20, 2004 issued in U.S. Appl. No. 10/140,096.
Office Action, dated Jun. 16, 2005 issued in U.S. Appl. No. 10/140,096.
Office Action, dated Mar. 28, 2006 issued in U.S. Appl. No. 10/140,096.
Office Action, dated Nov. 5, 2003 issued in U.S. Appl. No. 10/140,096.
Office Action, dated Jun. 4, 2004 issued in U.S. Appl. No. 10/344,863.
Office Action, dated Sep. 27, 2005 issued in U.S. Appl. No. 10/344,863.

* cited by examiner

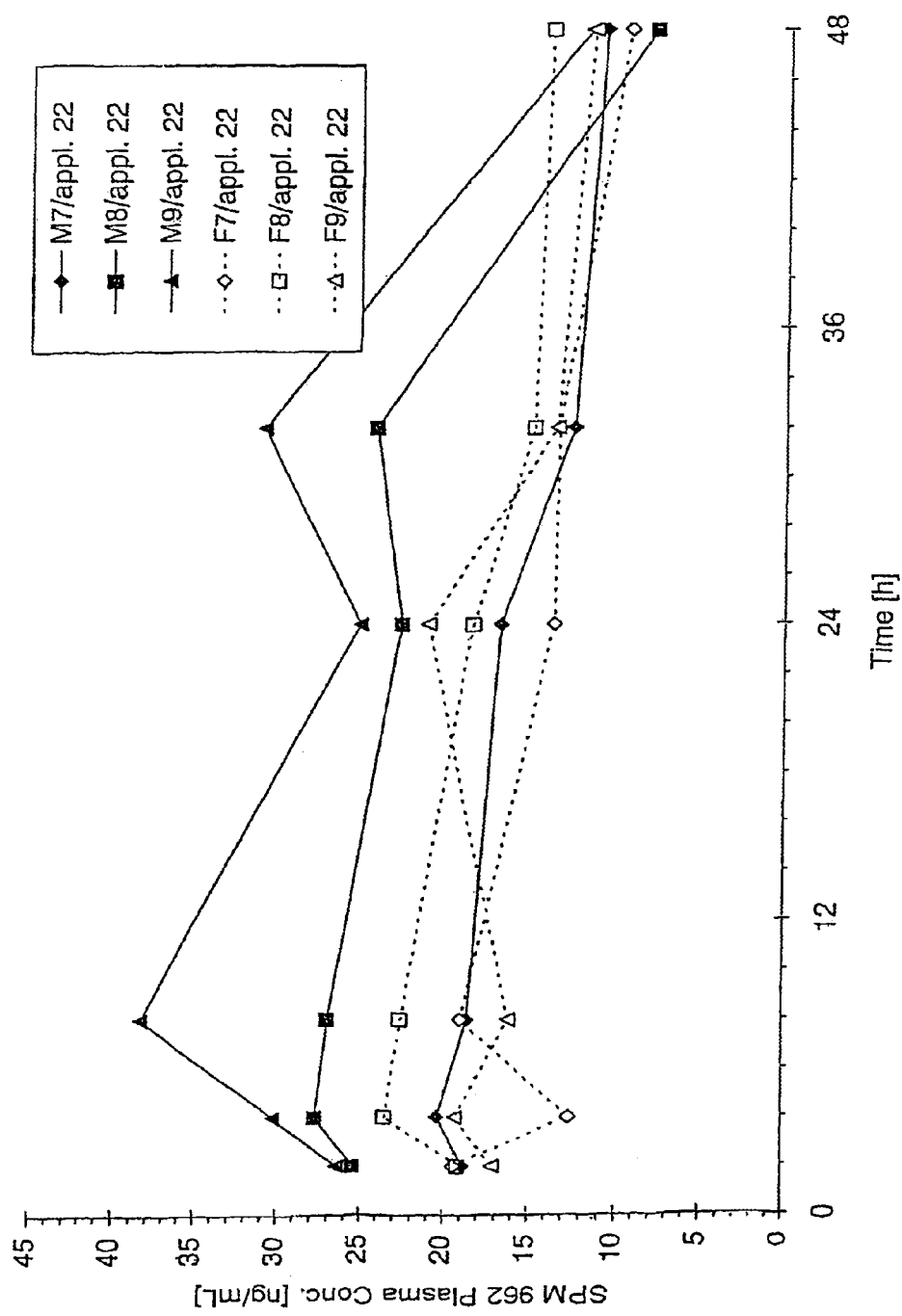

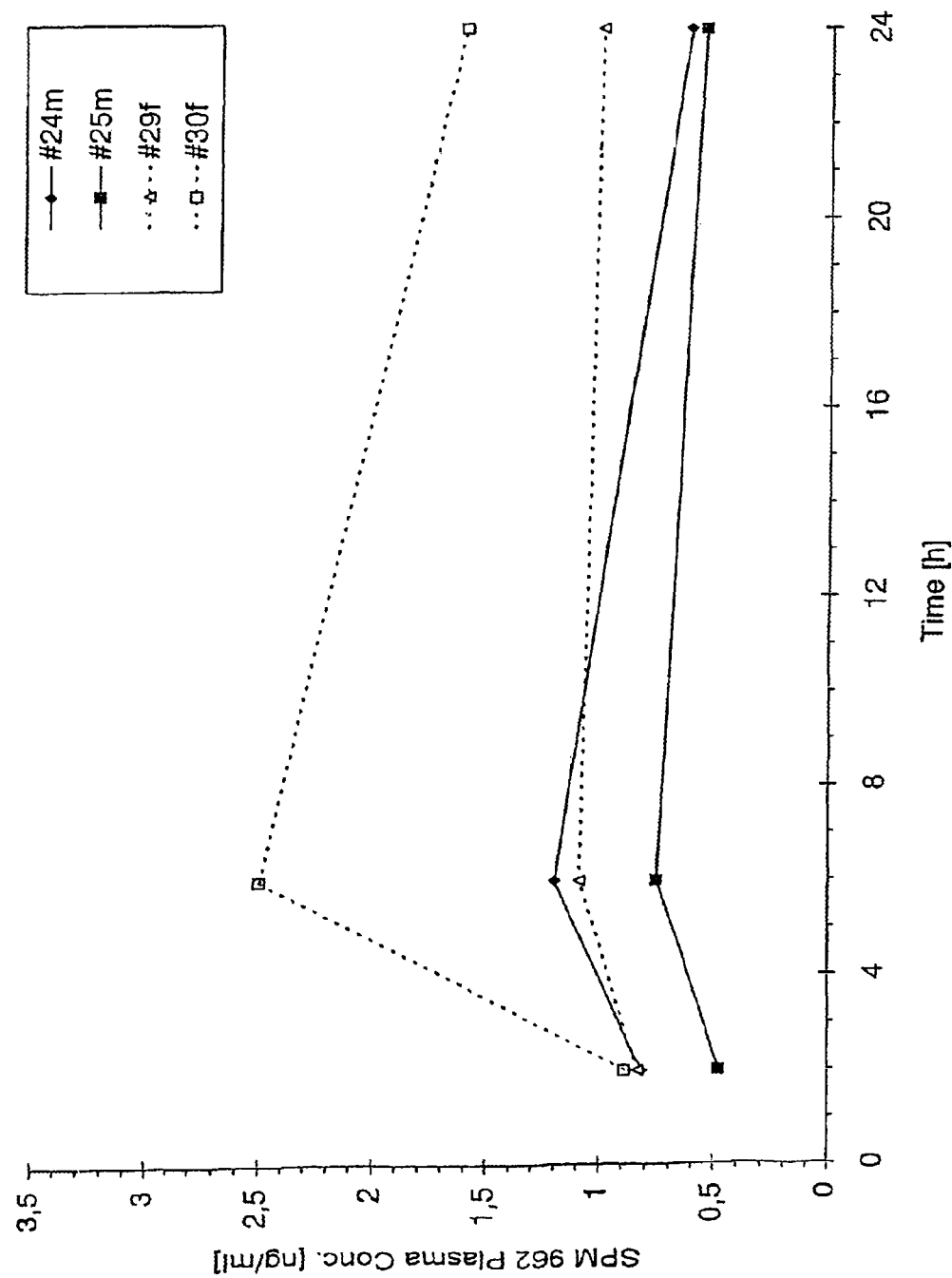

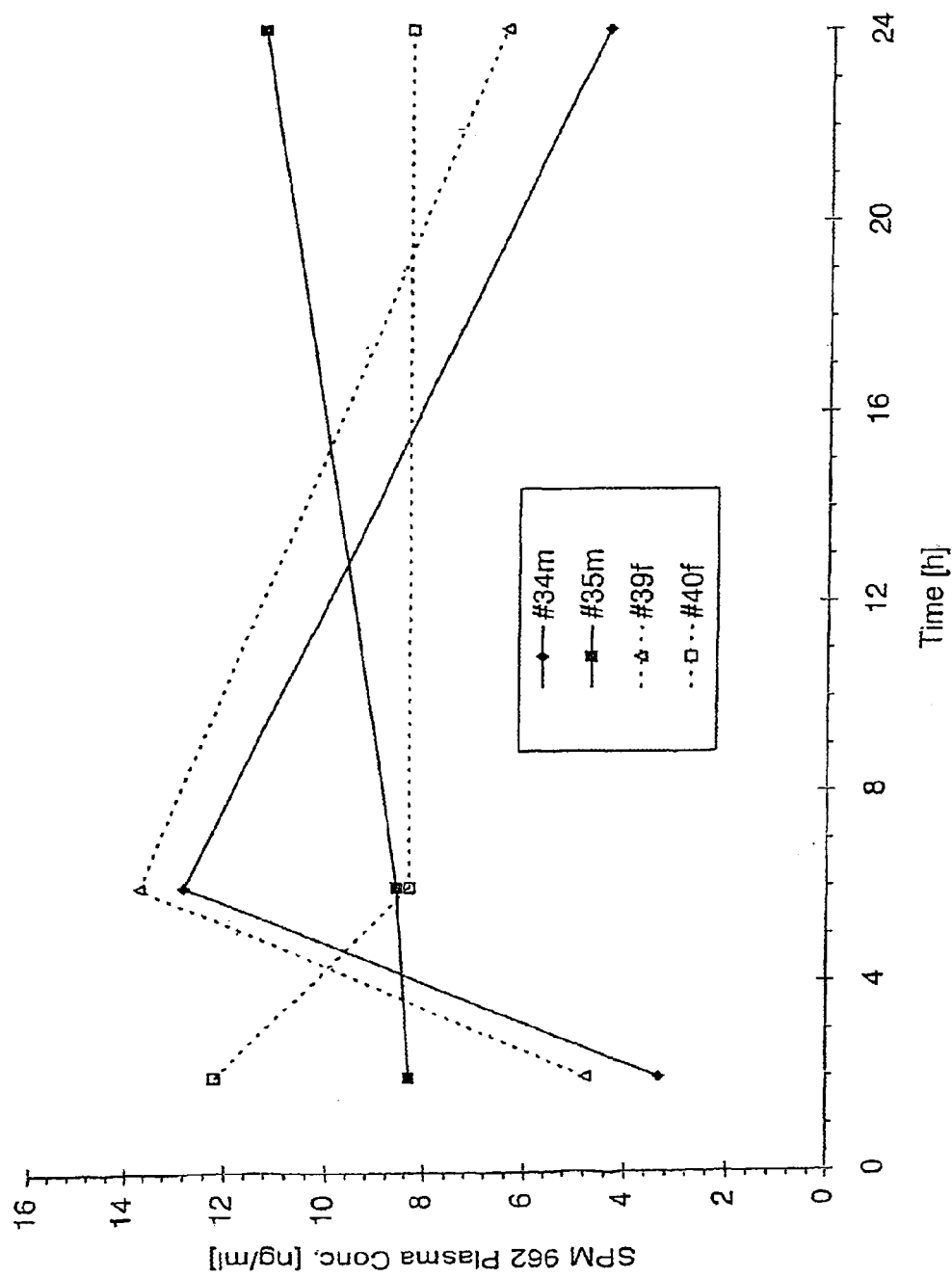

METHOD FOR PRODUCING A PHARMACEUTICAL COMPOSITION COMPRISING ROTIGOTINE

This application is a U.S. national stage filing under 35 U.S.C. §371 of International Application No. PCT/EP2001/09595 filed on Aug. 21, 2001, which claims priority of German Application No. DE 100 41 479.6 filed on Aug. 24, 2000. The disclosure of each of the applications identified in this paragraph is incorporated herein by reference in its entirety.

BRIEF DESCRIPTION OF THE INVENTION

This invention relates to a pharmaceutical composition for administering the dopamine agonist N-0923 (Rotigotine) in depot form.

Preferred implementations are in the form of oily suspensions containing the active agent N-0923 in its solid phase, as well as anhydrous pharmaceutical preparations of N-0923.

The invention further relates to the use of solid N-0923 for producing thermally sterilizable medications.

TECHNICAL BACKGROUND

N-0923 (rotigotine; S(-)-2-(N-propyl-N-2-thienylethylamino)-5-hydroxytetralin) is a potent and selective dopamine D2 agonist playing a significant role in the treatment of all diseases associated with a dopamine-related metabolic disorder such as Parkinson's disease and Restless Leg. Various attempts have been made in the past at administering N-0923 in therapeutically meaningful quantities.

It was found, however, that due to a distinct first-pass effect the bioavailability after oral administration is merely about 0.5% (Swart and Zeeuw, Pharmazie 47 (1992) 613), ruling out oral administration of N-0923.

Moreover, even when the substance is parenterally administered in an aqueous solution, it is rapidly eliminated. The half-time value of N-0923 after intravenous injection in monkeys in an aqueous solution is 52 minutes (Walters et al, Jr Pharmac Sci 83 (1994) 758) which in the case of an extended therapy would require for the patient an unacceptable frequency of administration.

Similarly, the subcutaneous injection of N-0923 in an aqueous solution (5% dextrose) was only effective for the very short time of 60-70 minutes (Belluzzi, Movement Disorders, 9.2 (1994) 147).

This leaves a need for non-oral forms of N-0923 medication so formulated as to significantly reduce the number of necessary therapeutic applications.

That is why in recent times transdermal systems have been developed. WO 94/07468 describes a diphasic matrix that may contain N-0923 as the active agent. WO 99/49852 discloses a monophasic matrix for the transdermal administration of N-0923.

Transdermal systems, however, are not suitable for all patients, and they pose a number of inherent problems. For example, numerous patients develop allergic reactions to such substances in the pads as adhesives, penetration enhancers and polymers.

Then, too, the acceptance of medicinal pads varies extensively as a function of national traditions and ethnocultural peculiarities.

Finally, with transdermal systems it is only marginally possible to select individualized dosages.

It is therefore the objective of this invention to introduce an alternative pharmaceutical formulation that includes a possible minimum of components while avoiding the above-described drawbacks of both transdermal and oral administration such as poor bioavailability, high frequency of administration, an immunogenic potential, possible toxicity and inadequately individualizable dosaging.

According to the invention, this objective has been achieved by the first-of-its-kind pharmaceutical formulation of the active agent N-0923 in depot form that is capable of continuously releasing the N-0923 over a duration of at least 24 hours.

In one preferred form of implementation the pharmaceutical formulation is an oily suspension containing the N-0923 in its solid phase.

In another preferred form of implementation, N-0923 is contained in an anhydrous formulation in the form of a crystalline salt which, when applied to a mammal, results in a continuous plasma level of 0.2-10 ng N-0923/ml blood over at least 24 hours.

Surprisingly, it is possible with this very simply structured formulation according to the invention to attain a therapeutically relevant N-0923 plasma level for as long as 48 hours. Moreover, the composition according to the invention can be produced easily and cost-effectively, it is biodegradable, non-toxic, biocompatible and well-tolerated.

As a particularly desirable feature, the pharmaceutical composition according to the invention contains but few, well-defined and well-tolerated additives.

Individualized quantification of the application volume or of the active-agent concentration, makes it very easy to adapt the dosage to the specific needs, symptoms and condition of the patient concerned.

The therapeutic compositions according to the invention thus lend themselves superbly to the treatment of diseases related to metabolic dopamine disorders such as Parkinson's disease or Restless Leg. Such treatment can be in the form of monotherapy but also in combination with other active agents or biocatalysts.

It was also found, rather unexpectedly, that when heated during the thermal sterilization process, N-0923 remains stable provided it is contained in the pharmaceutical compositions according to the invention in its solid phase. By contrast, dissolved N-0923 when heat-sterilized undergoes substantial thermal decomposition.

BRIEF DESCRIPTION OF THE DRAWINGS

FIG. 2 shows plasma concentrations of N-0923 after the subcutaneous administration of 12.5 mg N-0923 per kg body weight of the rat. The preparation was administered every 48 hours. The plasma levels of the individual animals were respectively recorded 2, 4, 8, 24, 32 and 48 hours after the 22nd application.

FIG. 3 shows the plasma concentrations of N-0923 in monkeys after 85 applications of 1 mg/kg N-0923 (FIG. 3A) and 4 mg/kg N-0923 (FIG. 3B) in the form of oily N-0923 crystalline suspensions.

DESCRIPTION OF THE INVENTION

Figure 1A:
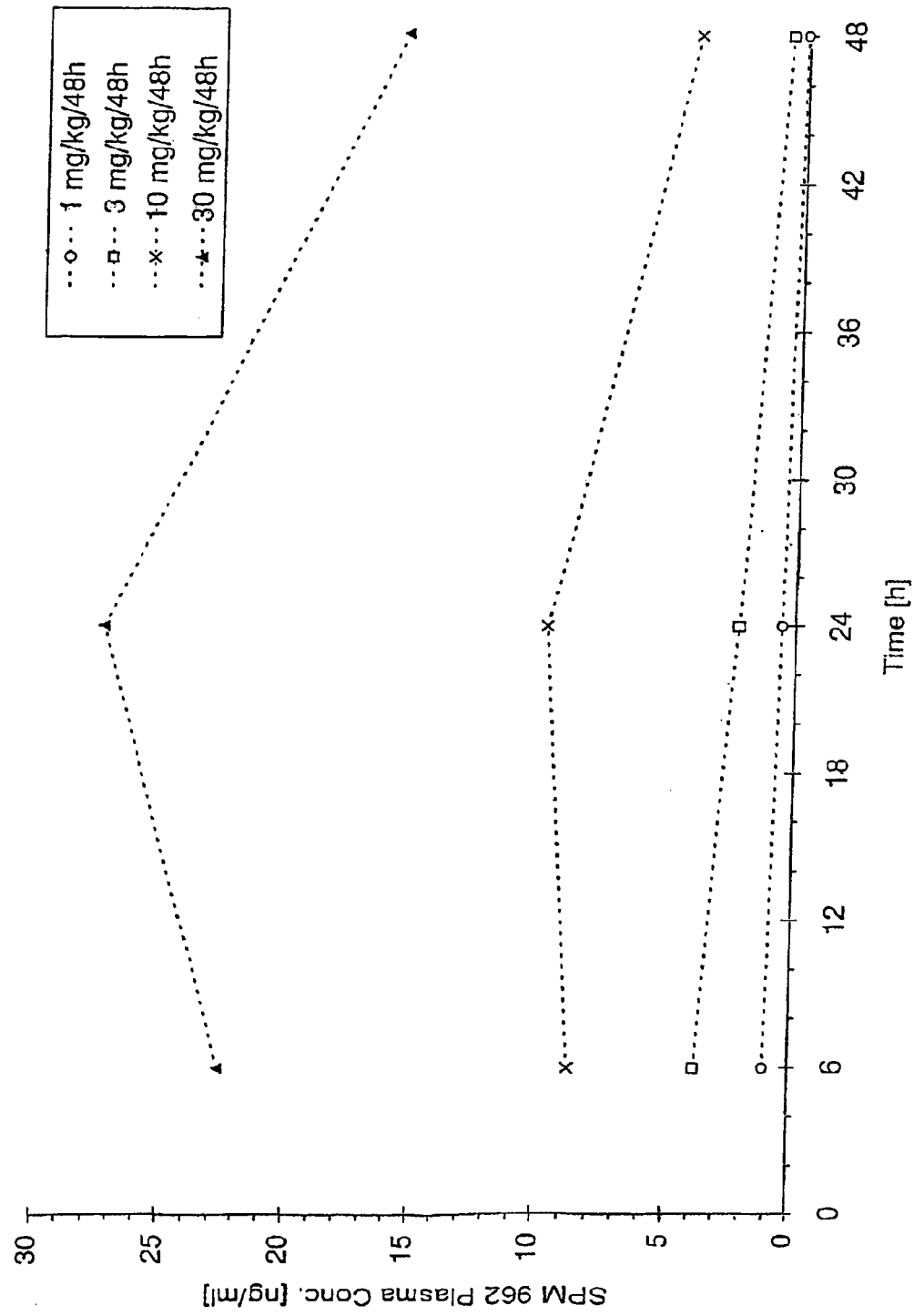
FIG. 1A shows averaged readings after the 2nd application, FIG. 1B after the 46th application.

This invention relates to pharmaceutical compositions containing N-0923 as the active agent, with the pharmaceutical composition being in depot form.

For the purpose of this patent application the term "depot form" or "depot" refers to a non-transdermal pharmaceutical formulation the application of which leads to a therapeutically effective N-0923 plasma level in the patient over a period of at least 24 hours. Preferred rotigotine plasma levels are between 0.2 and 10 ng/ml, especially between 0.3 and 5 ng/ml and ideally between 0.4 and 3 ng/ml.

The term "N-0923" refers to the substance 2-(N-propyl-N-2-thienylethylamino)-5-hydroxytetralin and to pharmaceutically acceptable salts thereof.

The term "N-0923 derivatives" refers to substituted 2-aminotetralins as claimed in U.S. Pat. No. 4,564,628.

Examples of depot forms include microparticles or microcapsules; lipid-based nanoparticles; active-agent complexes with, or embedded in, organic or inorganic substances such as gelatins, polyvinylpyrrolidone, carboxymethylcellulose or polyglutamic acid; emulsions or suspensions.

The microcapsules or microparticles can be produced by essentially conventional methods, for instance by microcapsulation or spray-drying on the basis of biodegradable polymers such as polylactide-polyglycolic copolymers (PLGA), for instance as described in EP 0 625 069.

In a preferred mode of implementation the depot is in the form of a suspension, preferably an oily suspension. In that suspension the N-0923 is suspended, essentially in its solid phase, in a liquid vehicle.

For the purpose of this patent application, the expression "essentially" means over 90%.

Preference is given to pharmaceutical compositions in which N-0923 is contained, in its solid phase, at over 95%, and especially at over 97% or over 99%.

For the purpose of this patent application, the term "oily suspension" refers to a dispersion in which the continuous phase (the "vehicle") is contained in the form of a liquid lipid.

For the purpose of this patent application the term "solid phase" refers to the presence of N-0923 as a solid. The N-0923 may be present in the form of free solids, for instance crystals or amorphous particles, or it may be bound to a suitable carrier material such as PLGA microparticles.

One preferred object of the invention consists of pharmaceutical formulations in which the N-0923 is largely insoluble. This leads to a protracted release of N-0923 from its solid phase after the formulation is administered to a live organism for instance in the form of a subcutaneous depot.

The expression "largely insoluble in the pharmaceutical formulation" means that, at room temperature, less than 10% of the therapeutic agent is present in the pharmaceutical formulation in a dissolved state.

Especially preferred are formulations in which N-0923 is soluble at less than 5%, better yet less than 3% and ideally less than 1%.

Therefore, one preferred object of this invention pertains to anhydrous N-0923-containing pharmaceutical compositions.

For the purpose of this patent application, the term "anhydrous" means a water content of less than 3%.

Particularly preferred formulations have a water content of less than 1% and ideally less than 0.5%.

After its application, the active agent is continually released from its solid phase over an extended period so that, in spite of the quick biological elimination of N-0923, a therapeutically effective plasma level of 0.1-15 ng/ml is obtained over a period of at least 24 hours, preferably more than 36 and most desirably more than 48 hours. Preferred plasma levels are 0.2-10 ng rotigotine/ml, desirably 0.3-5 ng/ml and ideally 0.4-3 ng/ml.

As an advantageous result, the frequency of N-0923 administration can be reduced to one single application per day or every two or three days.

One object of the invention is therefore a pharmaceutical formulation for the administration of N-0923 over a period of at least 24 hours and preferably of at least 36 or 48 hours.

This is achievable by converting N-0923 into a highly water-soluble, pharmaceutically acceptable salt that is not or only weakly soluble in aliphatic solvents and especially oils and is thus largely insoluble in a corresponding anhydrous formulation.

Examples of such pharmaceutically acceptable salts include the salts of inorganic or organic acids such as hydrochloride, hydrobromide, hydrogen sulfate, carbonic acids or alkane sulphonic acid, or salts with metal cations.

N-0923 hydrochloride is a particularly preferred example.

The free base of N-0923, however, is less suitable since it is relatively soluble in organic solvents and aliphatic hydrocarbons.

Preferred are pharmaceutical compositions in which the N-0923 is contained essentially in the form of free crystals or amorphous particles.

Particular preference is given to pharmaceutical depot forms containing N-0923 crystals.

N-0923 crystals are easily produced by recrystallizing the N-0923 salt in organic solvents, for instance as described in U.S. Pat. No. 4,564,628.

For example, crystalline N-0923 hydrochloride can be produced by first heating and dissolving N-0923 hydrochloride in methanol, stripping the methanol by distillation, dissolving the residue in acetone at over 50° C. and then allowing the N-0923 HCl to crystallize out over several hours at low temperatures. Further purification can be accomplished by recrystallization for instance in acetone or propanol.

The crystalline, hydrophilic N-0923 salts are finally introduced in anhydrous injectable formulations in which these salts are highly or largely insoluble.

Pharmaceutical formulations of this type may be based for instance on a continuous phase consisting of pharmaceutically acceptable, liquid glyceric fatty acid esters, lipidols, aliphatic hydrocarbons (e.g. paraffin) or hydrophobic liquid silicone, in which the N-0923 salt, for instance N-0923 hydrochloride, is introduced in crystalline form. From this lipid-containing or hydrophobic phase the hydrophilic crystalline N-0923 salt, when applied on the patient, will be released only slowly, i.e. in retarded fashion.

Therefore, in a preferred form of implementation the invention relates to an anhydrous, hydrophobic pharmaceutical composition that contains solid, preferably crystalline rotigotine salt and, with application intervals of at least 24 hours, allows for a continuous plasma level of between 0.2 ng and 10 ng rotigotine/ml to be maintained over the entire length of the administration period.

The N-0923 dose administered and thus the plasma level can be controlled by quantizing the concentration of the active agent in the formulation and also by selecting the appropriately measured injection volume.

That volume can be varied over a wide range from 5 to 1500 μl, permitting particularly easy, individualized dosaging in adaptation to the specific situation of the parent.

Preferred application volumes range from 10 to 500 it or from 100 to 10004

The range of the N-0923 concentration is primarily determined by the intended pharmacological effect of the N-0923 after the depot is applied. For N-0923, a suitable concentration range is 0.01-10% (w/v), or preferably 0.02-5% and ideally 0.1-2%.

Suitable daily dosages of rotigotine may be 0.5-40 mg, preferably 1-20 mg, better yet 2-15 mg and ideally 2-10 mg.

In one form of implementation the pharmaceutical composition is an oily suspension that contains N-0923 in its solid phase and whose own continuous phase is a lipid.

Pharmaceutically acceptable lipids include for instance vegetable oils such as almond oil, olive oil, poppy oil, peanut oil or sesame oil, higher-level fatty acids such as oleic acid, as well as fatty-acid mono-, di- or tri-esters from mono- or polyols such as isopropanol, 1,3-propanediol, glycerol, 1,2-butanediol or 1,2,3-butanetriol.

In one preferred form of implementation the pharmaceutical preparation is an oily suspension whose vehicle essentially consists of polyol fatty acid esters.

For the purpose of this patent application the term "polyol fatty acid esters" also subsumes mixtures of various polyol fatty acid esters.

Polyol fatty acid esters preferred for the polyol component are polyols with two to four C-atoms and a variable number of hydroxy groups. Suitable examples include 1,3-propanediol, glycerol, 1,2,3-butanetriol, 1,2,4-butanetriol or 1,3-butanediol.

Especially preferred for the polyol component of the continuous phase are glycerol, 1,3-propanediol and/or 1,3-butanediol.

The overall esterification level of the polyol fatty acid esters of the continuous phase is preferably 80-100% and ideally 90-100%.

The preferred chain length of the fatty acids in said polyol fatty acid esters of the vehicle is between 6 and 22 C-atoms and especially between 6 and 14 C-atoms.

The vehicle preferably contains 60% saturated fatty acids or, most desirably, over 90% saturated fatty acids.

Particularly preferred as the key vehicle component are medium-chain triglycerides (MCTs) as described in pharmacopoeias and primarily containing saturated fatty acids with chain lengths of 8-10 C-atoms.

Therefore, one preferred object of this invention covers pharmaceutical depot forms of N-0923 configured as an oily suspension and encompassing a vehicle that consists essentially of MCTs.

MCTs are well-defined substances that have worked well in systemic forms of administration. MCTs have the advantage of being biodegradable and non-irritating, with excellent physiochemical properties for use even in injectable forms of medication. MCTs are therefore particularly well-suited to serving as a vehicle for the pharmaceutical compositions according to the invention.

One example is the commercially available triglyceride caprylic acid/capric acid ester marketed under the tradename Miglyol 812® (by Condea).

The proportional amount of the continuous phase (of the vehicle) in the pharmaceutical composition is a function of the concentrations of the active agent, the wetting agent and any other adjuvants. It is typically 75%, preferably 88-99.8%, and a particularly suitable concentration is 94-99%.

In a preferred form of implementation of the invention, the pharmaceutical composition is an oily suspension that also contains a wetting agent. The term "wetting agent" refers to a substance that reduces the interfacial tension between the surface of the vehicle and that of the active agent.

Those skilled in the art are familiar with state-of-the-art wetting agents. Without limiting patent protection, the following are named as suitable examples:

Condensation products from polyols and carbonic acids such as the fatty acid esters of isopropanol, glycerol, 1,3-butanediol, 1,2,4-butanetriol, 1,2,3-butanetriol, 1,3-propanediol, sucrose, sorbitan, propylene glycol, polyoxyethylene, polyoxyethylene sorbitol, or dextrin.

Condensation products from polyols and long-chain alcohols such as polyoxyethylene cetanol or polyoxypropylene hexadecanol.

Preferred wetting agents for the pharmaceutical compositions according to the invention consist essentially of polyol (polyhydroxy) fatty acid esters.

In a preferred form of implementation the wetting agent contained in the pharmaceutical composition according to the invention consists of polyol fatty acid esters with a monoester component of over 60% and preferably over 90%.

These polyol fatty acid esters preferably contain polyols with two to six C-atoms, for example glycerol, 1,3-butanediol, 1,3-propanediol, 1,2,3-butanetriol, 1,2,4-butanetriol, isopropanol, sucrose or sorbitan.

Particularly preferred wetting agents for the pharmaceutical compositions according to the invention are polyol fatty acid esters containing glycerol or 1,2,3-butanetriol.

The preferred chain length of the fatty acids in said polyol fatty acid esters of the wetting agent is 6 to 22 C-atoms and especially 6 to 14 C-atoms.

The polyol fatty acid monoesters of the wetting agent preferably contain over 60% and ideally over 90% saturated fatty acids.

In another preferred form of implementation of the invention the wetting agents employed are glycerol or 1,2,3-butanetriol esterized with saturated fatty acids having 6-14 C-atoms.

Particularly preferred wetting agents are commercially available products such as glycerol monocaprylate (Imwitor 308 by Condea).

Special preference is given to pharmaceutical compositions containing as their wetting agent glycerol monolaurate, commercially available for instance under the trade name Imwitor 312®. Glycerol monolaurate is a well-documented substance approved in Germany as a food additive and found to be particularly suitable for use in the depot forms according to the invention.

Therefore, a particularly preferred object of this invention is a pharmaceutical composition containing N-0923 in its solid phase, a liquid vehicle and a wetting agent, said wetting agent consisting essentially of glycerol laurate and/or glycerol monocaprylate.

In another preferred form of implementation the rotigotine-containing anhydrous pharmaceutical composition is free of any phosphatides. The inventor was surprised to find that adding lecithin, described in the literature as a wetting agent, cancels the retarding effect of the crystalline rotigotine-containing formulation. Therefore, one aspect of the invention is an anhydrous pharmaceutical retardant that contains crystalline rotigotine salt but is devoid of any lecithin.

The concentration range of the wetting agent depends on the amount of the active agent. The concentration of the wetting agent must be high enough to ensure proper wetting of the active-agent particles which can be established in simple fashion using suitable tests with which those skilled in the art are familiar. On the other hand, the concentration of the wetting agent selected must be held below the point where the wetting agent would precipitate in crystal form.

A suitable concentration range (in w/w) for the wetting agent is 0.02-10%, preferably 0.1-5% and most desirably 0.5-2.5%, with the concentration of the wetting agent in each case adapted to the concentration of the active agent.

The pharmaceutical composition according to the invention may also contain additives and adjuvants with which the pharmacologist is familiar. Such additives may be lipid-soluble antioxidants such as vitamin E whenever said compositions comprise for instance a vehicle and/or wetting agent that contains unsaturated fatty acids. Where appropriate, the pharmaceutical composition may also contain thickeners.

In another aspect of the invention, the pharmaceutical composition according to the invention contains the following components:
(a) N-0923 in its solid phase,
(b) a vehicle essentially consisting of polyol fatty acid esters with an overall esterification level of over 80%,
(c) a wetting agent essentially consisting of polyol fatty acid esters with a monoester component of over 60%.

Appropriate vehicles and wetting agents for this purposes are those described and discussed further above.

Another aspect of this invention covers the production of N-0923 depot forms.

A depot form of that type can be produced in particularly simple and practical fashion by suspending solid N-0923 in a liquid, oily phase. The vehicle used for the oily phase is a polyol fatty acid ester, preferably a triester of a polyol with two to four C-atoms, with a fatty-acid chain length of 6 to 14 C-atoms, for instance a medium-chain triglyceride. A wetting agent that may be added is a polyol fatty acid monoester, preferably a monoester of a polyol with two to six C-atoms, with a fatty acid having a chain length of 6 to 14 C-atoms, for instance glycerin monolaurate. In a preferred form of implementation of this production method the N-0923 is used in the crystalline state and especially as a crystalline hydrochloride salt, and the composition is produced without the addition of water.

The following are practical concentrations (in w/w) for the production, per this invention, of an N-0923 depot form: For N-0923, 0.01-10%, preferably 0.02-5% and ideally 0.1-2%; for the vehicle, 75-99.9%, preferably 88-99.8% and ideally 94-99%; and for the wetting agent, 0.02-10%, preferably 0.1-5% and ideally 0.5-2.5%.

Another aspect of this invention is an essentially anhydrous pharmaceutical composition containing N-0923 preferably in crystalline form.

The pharmaceutical compositions according to the invention are all suitable for mucosal i.e. for instance nasal administration or for parenteral application.

The compositions are particularly well suited to administration by injection whether by means of conventional syringes or by needle-less injection systems. Examples of such needle-less injection systems are described in U.S. Pat. Nos. 5,840,062 and 4,913,699. The injection can be performed using any prior-art application mode for depot forms, whether subcutaneous, intracutaneous, intramuscular or intracranial, for instance intraventricular.

The preferred administration is subcutaneous, intracutaneous or intramuscular, with subcutaneous application being especially preferred.

Surprisingly, it is possible with the very simply structured formulations according to the invention to reach an N-0923 plasma level that is therapeutically significant over 48 hours. The bioavailability of the pharmaceutical composition according to the invention is more than 70% for N-0923 and the active-agent plasma levels are in a largely linear relation to the dose introduced in the body (see FIG. 4).

The pharmaceutical compositions according to the invention are therefore superbly suitable for the chronic treatment of diseases associated with a dopamine-metabolic disorder. Examples of such diseases include Parkinson's disease and the Restless Leg syndrome.

For the treatment the formulations according to the invention can be applied in the form of monotherapy or in combination with other antiparkinsonian agents.

The term "antiparkinsonian agent" refers to any active agent that is capable of favorably influencing a pathologically changed dopamine metabolism and/or able in any other way to reduce or prevent the progression or existence of Parkinson's disease and/or to alleviate the symptoms accompanying Parkinson's disease.

Those skilled in the art are familiar with antiparkinsonian agents. Named below, without limiting patent protection, are examples of suitable additional active agents: Members of the group of metabolic dopamine precursors, dopamine receptor agonists, dopamine transport blockers, MAO inhibitors, muscarine receptor antagonists, glutamate receptor antagonists, catechol-O-methyltransferase blockers, neurotrophins, immunophilin ligands, histamine antagonists, antioxidants, glutathione transferase activators, anti-apoptosis agents or calcium antagonists.

Suitable representative members include in particular levodopa, methyldopa, biperiden, pargyline, rasagiline, selegiline, lisuride, pergolide, bromocriptine, cabergoline, benzatropine, ropinirole, amantadine, memantines, trihexyphenidyl, diphenhydramine, dihydroergocryptine, tolcapone, entacapone, metixene, procyclidine, budipine, bornaprine, pramipexole, glial cell line-derived neurotrophic factor (GDNF) and the brain-derived neurotrophic factor (BDNF).

Said active agents may be administered jointly with N-0923 in the pharmaceutical preparation according to the invention or they may be applied in a separately injectable or non-injectable formulation, for instance as a 'kit of parts'. In that context, the added antiparkinsonian agent may itself be formulated in retarded or nonretarded form.

This invention has provided the first-ever injectable N-0923 depot formulations capable of releasing N-0923 in therapeutically effective quantities over a time span of at least 24 hours. Therefore, another aspect of this invention is the use of N-0923 for producing a depot medicament.

The pharmaceutical compositions according to the invention as described in this patent application also lend themselves to the administration of N-0923 derivatives described in U.S. Pat. No. 4,564,628. Therefore, another object of this invention includes pharmaceutical depot forms of N-0923 derivatives as well as the use of N-0923 derivatives for producing depot medications.

Another aspect of this invention is the use of N-0923 in its solid phase for producing a thermally sterilizable medicament. It was unexpectedly found that N-0923 in its solid phase remains stable when heated during the sterilization process. By contrast, dissolved N-0923 undergoes a substantial thermal decomposition during the autoclaving (see implementation example 4).

One preferred object of this invention is the use of crystalline N-0923, especially in the form of hydrochloride salt, for producing a thermally sterilizable medicament.

For the purpose of this patent application the term "thermally sterilizable medicament" refers to a pharmaceutical formulation in which, when heated to 121° C. at 0.2 mPa over a period of 20 minutes, the active agent will decompose by less than 1%.

Another object of this invention is the production of a sterile pharmaceutical composition containing N-0923 by autoclaving a pharmaceutical preparation that contains N-0923 in its solid phase. As an example hereof, a pharmaceutical formulation according to the invention is autoclaved for 20 minutes at 121° C. and 0.2 mPa.

In a preferred implementation thereof, the N-0923 is in the form of a crystalline hydrochloride salt contained for instance in an oily suspension.

Another aspect of the invention is the provision of a kit for the treatment of Parkinson's disease or Restless Leg syndrome, comprising a pharmaceutical composition according to the invention and an injection device.

The injection device may be an injection system yet to be filled with the pharmaceutical composition or an injection system prefilled with the pharmaceutical composition according to the invention. The injection device may be equipped with a conventional cannula or, alternatively, it may be designed to serve as a needle-less injection system.

Also covered by the invention is a kit containing several dosages of the pharmaceutical composition according to the invention as well as several injection devices, serving for instance as a week's or a month's supply.

Another aspect of the invention is a kit comprising a pharmaceutical composition according to the invention and configured for the oral or transdermal administration of N-0923 or of some other antiparkinsonian agent.

Combining an injectable and an oral form of administration in one kit may be useful for instance in preventing or bridging an excessive drop of the plasma level between the exhaustion of one depot and the application of a new depot.

Therefore, one preferred implementation is a kit containing an injectable depot form of N-0923 and an oral, fast-acting formulation of an antiparkinsonian agent.

One example of fast-acting orally administered doses is described for instance in EP 651 997.

Another preferred object of the invention is a kit comprising the pharmaceutical N-0923 preparation according to the invention and a transdermal form of administration of N-0923.

The following examples serve to illustrate this invention:

IMPLEMENTATION EXAMPLES

1. Producing and Crystallizing N-0923

Crystalline N-0923 is produced and crystallized as described in U.S. Pat. No. 4,564,628. Alternatively, crystalline N-0923 can be produced by first heating and dissolving N-0923 hydrochloride in methanol, then stripping the methanol by distillation, dissolving the residue in acetone at over 50° C., then allowing the N-0923 HCl to crystallize out for several hours at low temperatures. Further purification can be obtained by recrystallization for instance in acetone or propanol.

2. Producing an N-0923 Suspension Containing 1% N-0923 and 1% GML (a) Producing the Continuous Phase 1411.2 g Miglyol 812 (triglyceride caprylic acid/capric acid ester) was weighed into a Duran vial. 14.4 g Imwitor 312 (glycerol monolaurate, GML) was added to the Miglyol and then heated for 30 minutes to 80° C. under simultaneous agitation. The clear solution was cooled down to room temperature and filtered.

(b) Producing the Suspension 1188 g of the solution produced per (b) above was transferred into a lab-type glass reactor, 12 g of N-0923 was added and homogenized in a nitrogen atmosphere for 10 minutes using an Ultraturrax at 10,000 RPM. With the Ultraturrax running (at 2,000 RPM), the suspension was filled into brown glass vials.

3. Production of an N-0923 Suspension Containing 0.5, 1.5 and 2% N-0923 and 0.5%, 1% or 1.5% GML The suspension was produced as described in [1.] implementation example 2 above except with suitably modified quantities.

4. Thermal Sterilization of N-0923

A 0.6% aqueous solution of N-0923 hydrochloride (preparation I) and a 1% N-0923 suspension per implementation example 2 (preparation II) were autoclaved for 20 minutes at 120° C. and 0.2 Pa. In addition, a 0.5% aqueous N-0923 solution (preparation III) was autoclaved in a nitrogen atmosphere. Subsequently the decomposition rates were determined by photometry.

It was found that in the autoclaving of the aqueous solutions of preparations 1 and III, 1.5% of the N-0923 had in each case thermally disintegrated into decomposition products. By contrast, preparation II had decomposed by less than 0.5%.

5. Release of N-0923 from the Depot Per this Invention in a Rat

Sprague-Dawley rats were given subcutaneous bolus injections of an oily N-0923 crystalline suspension of the following composition:

| N-0923: | 0.5 or 1% |
|---|---|
| Imwitor 312: | 1% |
| Miglyol 812: | to 100% |

The following dosages were applied every 48 hours:

1 mg/kg (0.2 ml/kg of a 0.5% suspension)
3 mg/kg (0.6 ml/kg of a 0.5% suspension)
10 mg/kg (1 ml/kg of a 1% suspension)
30 mg/kg (3 ml/kg of a 1% suspension)

Figure 1B:
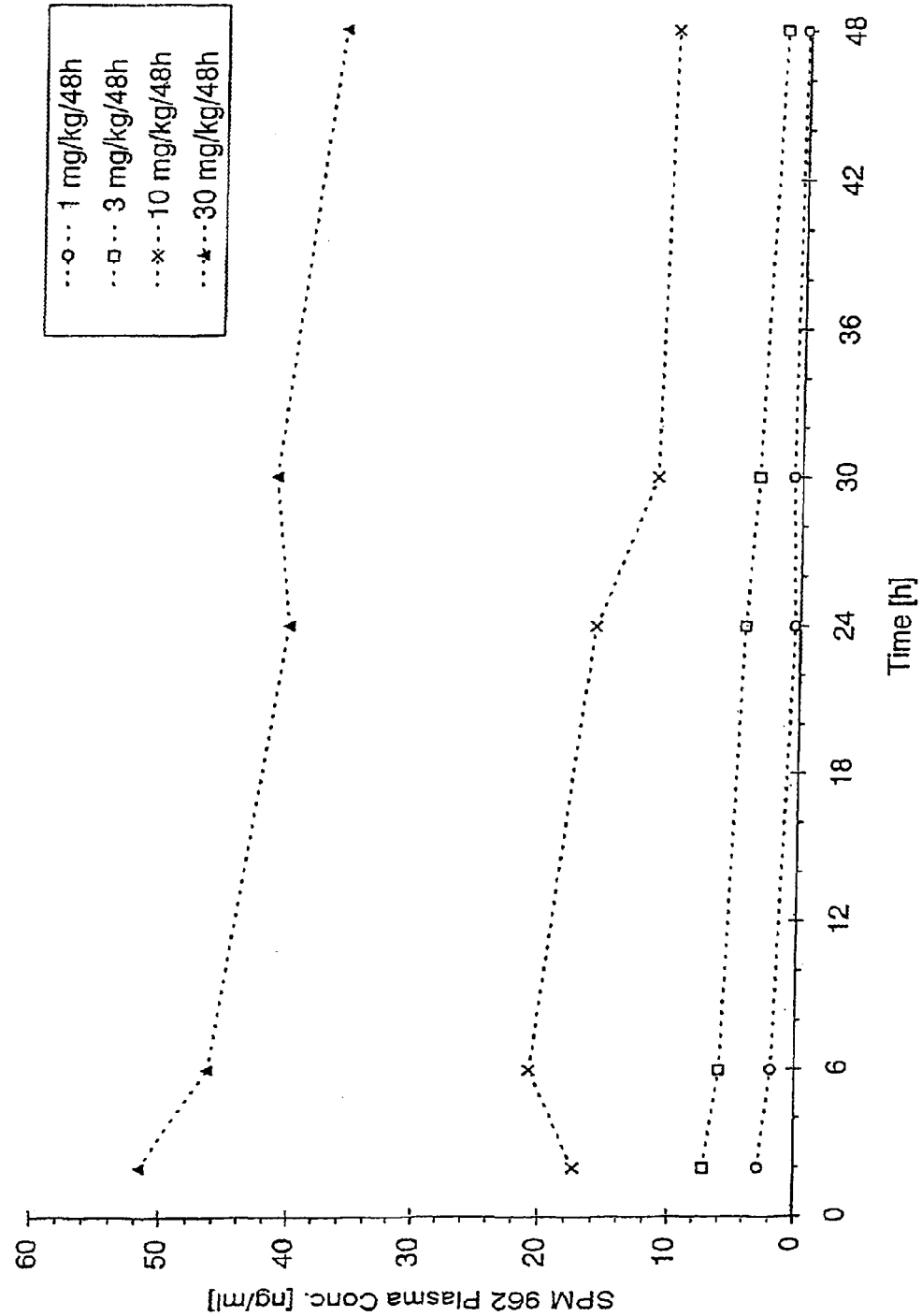
FIG. 1 shows plasma concentrations of N-0923 after the subcutaneous administration in rats of four different dosages in an oily crystal suspension. The preparation was administered every 48 hours over several weeks.

6, 24 and 48 hours after the 2nd and 46th administration plasma samples were taken and the N-0923 concentration was analyzed using LC-MS-MS. The readings from 6 animals were averaged. The results are shown in FIG. 1.

6. Release of N-0923 from the Depots Per this Invention in the Rat

The test conditions were identical to those in implementation example 5 except that every 48 hours a dose of 12.5 mg N-0923 per kg body weight was applied.

Readings were taken 2, 4, 8, 24, 32 and 48 hours after the 22nd application and were quantified. The plasma levels of the individual animals are shown in FIG. 2.

7. Release of N-0923 from the Depots Per this Invention in the Monkey

Cynomolgus monkeys were given daily subcutaneous bolus injections of oily N-0923 crystalline suspensions of the following composition:

| N-0923: | 0.5 or 1% |
|---|---|
| Imwitor 312: | 1% |
| Miglyol 812: | to 100% |

The application was performed daily in dosages of 0.25, 1 and 4 mg/kg. 2, 6 and 24 hours after the 3rd and 85th application plasma samples were taken and analyzed using LC-MS-MS.

Figure 4:
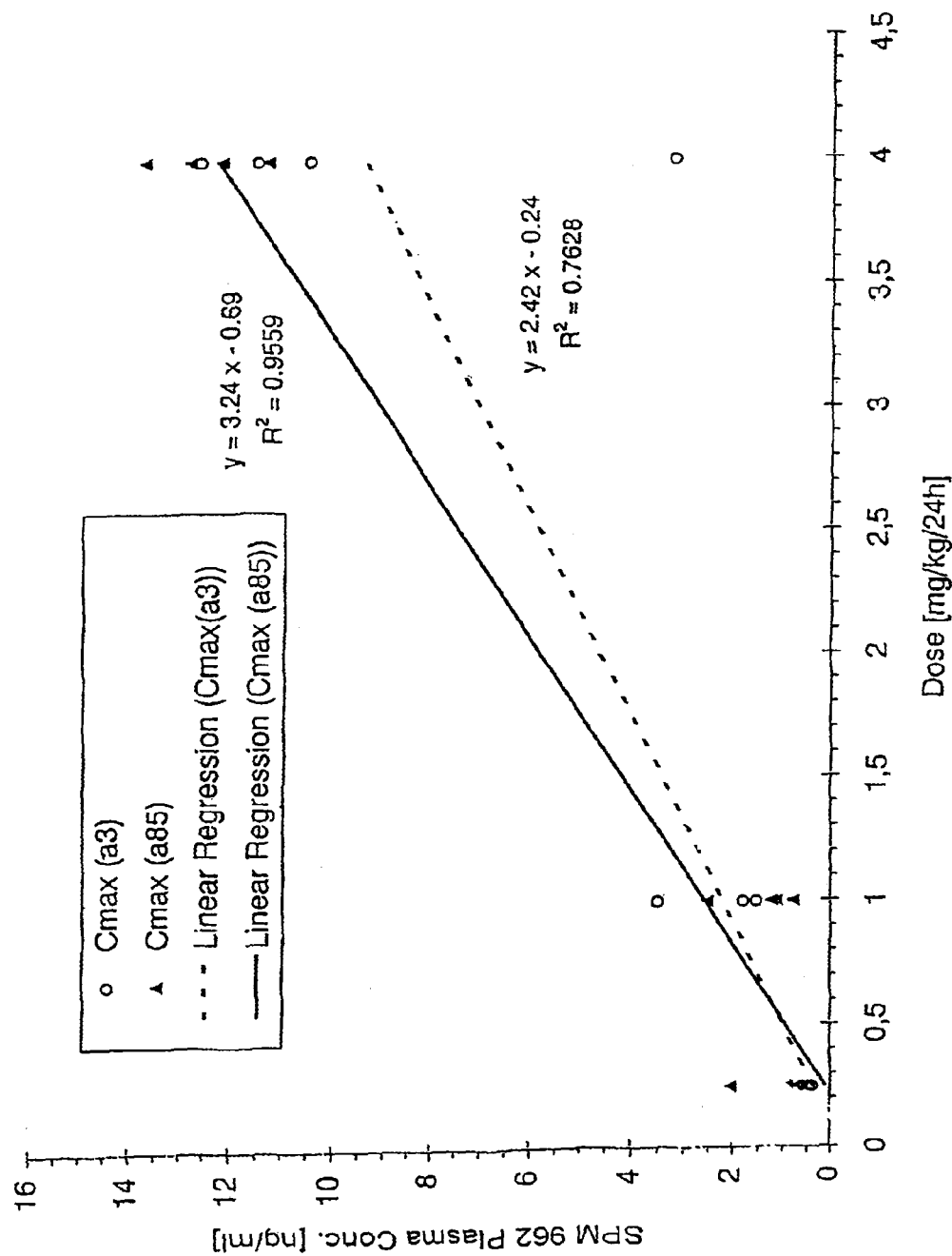
FIG. 4 illustrates the correlation between an applied N-0923 dose in the form of oily crystalline suspensions and the maximum plasma level after 3 and, respectively, 85 daily applications in monkeys.

FIG. 3 shows the readings for the individual animals. FIG. 4 shows the relationship between the dose applied and the resulting maximum plasma concentrations.

The invention claimed is:

1. A method for producing an injectable pharmaceutical composition, comprising
    preparing an oily suspension of solid-phase rotigotine or a pharmaceutically acceptable salt thereof in a pharmaceutically acceptable hydrophobic liquid phase that comprises a wetting agent free of phosphatides; and
    thermally treating said oily suspension to provide a sterile depot suspension of said rotigotine or salt thereof.

2. The method of claim 1, wherein less than 1% by weight of the rotigotine or salt thereof decomposes during the thermal treatment.

3. The method of claim 1, wherein the solid-phase rotigotine or salt thereof is in crystalline form.

4. The method of claim 3, wherein the crystalline rotigotine is in a form of a hydrochloride salt.

5. The method of claim 1, wherein over 95% by weight of rotigotine in the composition is in solid phase.

6. The method of claim 1, wherein less than 0.5% by weight of the rotigotine decomposes while thermally treating said oily suspension of rotigotine.

7. The method of claim 1, wherein said thermally treating comprises autoclaving the composition.

8. The method of claim 1, wherein said thermally treating is performed in a nitrogen atmosphere.

9. The method of claim 1, wherein the oily suspension contains less than 3% water.

\* \* \* \* \*

UNITED STATES PATENT AND TRADEMARK OFFICE
CERTIFICATE OF CORRECTION

| | | |
|---|---|---|
| PATENT NO. | : 8,604,076 B2 | Page 1 of 1 |
| APPLICATION NO. | : 10/344884 | |
| DATED | : December 10, 2013 | |
| INVENTOR(S) | : Steven Rimpler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1101 days.

In the Specification

Column 1, line 39, replace "Jr" with --J--.

Column 4, line 64, replace "500 it" with --500 µl--.

Column 4, line 65, replace "10004" with --1000 µl--.

Column 10, line 15, replace "1" with --I--.

Signed and Sealed this
Fifth Day of May, 2015

Michelle K. Lee
*Director of the United States Patent and Trademark Office*